(12) United States Patent
Gundu et al.

(10) Patent No.: US 9,180,110 B2
(45) Date of Patent: *Nov. 10, 2015

(54) PHARMACEUTICAL COMPOSITIONS OF FENOFIBRATE

(71) Applicant: WOCKHARDT RESEARCH CENTRE, Maharashtra (IN)

(72) Inventors: Ramakant Kashinath Gundu, Maharashtra (IN); Narayanan Murali, Tamilnadu (IN); Girish Kumar Jain, Dehli (IN)

(73) Assignee: Wockhardt Ltd., Bandra East, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/470,104

(22) Filed: Aug. 27, 2014

(65) Prior Publication Data

US 2014/0364497 A1    Dec. 11, 2014

Related U.S. Application Data

(63) Continuation-in-part of application No. 12/528,628, filed as application No. PCT/IB2008/000405 on Feb. 23, 2008, now Pat. No. 8,852,635.

(30) Foreign Application Priority Data

Feb. 26, 2007    (IN) .......................... 372/MUM/2007

(51) Int. Cl.
*A61K 9/16* (2006.01)
*A61K 31/216* (2006.01)
*A61K 9/20* (2006.01)

(52) U.S. Cl.
CPC ............ *A61K 31/216* (2013.01); *A61K 9/2031* (2013.01); *A61K 9/1641* (2013.01)

(58) Field of Classification Search
CPC .................................................... A61K 31/216
USPC ........................................................ 514/543
See application file for complete search history.

(56) References Cited

U.S. PATENT DOCUMENTS

2004/0058009 A1    3/2004   Ryde et al.

FOREIGN PATENT DOCUMENTS

| CA | 2214895 A1 | 9/1998 |
|----|-----------|--------|
| EP | 1364646 A | 9/2003 |
| WO | WO96/21439 A | 7/1996 |
| WO | WO02/11699 A1 | 2/2002 |

*Primary Examiner* — Jake Vu
(74) *Attorney, Agent, or Firm* — Bio Intellectual Property Services LLC (Bio IPS); O. (Sam) Zaghmout

(57) ABSTRACT

The invention relates to pharmaceutical compositions comprising unmicronized fenofibrate in admixture with a wetting agent and one or more pharmaceutically acceptable excipients, wherein the admixture is not comicronized before processing. The invention also relates to processes for the preparation of such compositions.

7 Claims, No Drawings

PHARMACEUTICAL COMPOSITIONS OF FENOFIBRATE

CROSS-REFERENCE TO RELATED APPLICATIONS

This application is a continuation-in-part of U.S. patent application Ser. No. 12/528,628, filed on Jun. 24, 2010, which entered the National Phase of Serial No. PCT/IB08/00405, filed Feb. 23, 2008, which claims a priority to Indian application 372/MUM/2007, filed Feb. 26, 2007. The entire disclosure of these prior applications are hereby incorporated by reference.

FIELD OF THE INVENTION

The invention relates to pharmaceutical compositions comprising unmicronized fenofibrate in admixture with one or more wetting agents and one or more pharmaceutically acceptable excipients, wherein the admixture is not comicronized before processing. The invention also relates to processes for the preparation of such compositions.

BACKGROUND OF THE INVENTION

Fenofibrate is a lipid-regulating agent and belongs to the family of fibrates or fibric acid derivatives. It is indicated as an adjunctive therapy to diet for the treatment for adult patients with very high elevations of serum triglyceride levels who are at risk of pancreatitis and who do not respond adequately to dietary control. It is particularly useful for the treatment of adult endogenous hyperlipidemia, hypercholesterolemia and hypertriglyceridemia. It is commercially available as oral capsules containing micronized fenofibrate in the strengths of 67 mg, 134 mg and 200 mg Fenofibrate is practically insoluble in water and exhibits a low rate of dissolution in aqueous media that results in inadequate bioavailability after oral ingestion. This low rate of dissolution of fenofibrate in aqueous media is also found in gastrointestinal fluids. Chemically, fenofibrate is 2-[4-(4-Chlorobenzoyl) phenoxy]-2-methylpropanoic acid 1-methylethyl ester of Formula I. Several methods of increasing the rate of dissolution of drugs having low solubility in water and other aqueous media have been disclosed in the prior art.

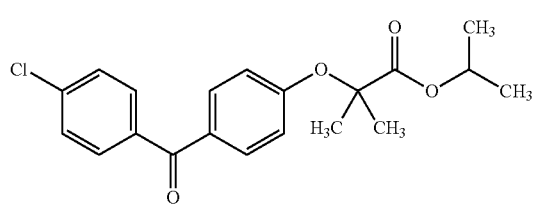

Formula I

U.S. Pat. Nos. 5,145,684; 6,375,986; 6,969,529; and 6,592,903 disclose nanoparticulate compositions of fenofibrate.

U.S. Pat. Nos. 6,277,405; 6,652,881; 7,037,529; 7,041,319; 6,589,552; 6,531,158 and U.S. Patent Application Nos. 20040057998; 20040058005 and 2004137055 disclose micronized fenofibrate compositions.

U.S. Pat. Nos. 4,895,726, 5,880,148 and U.S. Application No. 20040071771 describe co-micronizing the fenofibrate with surface-active agents.

U.S. Pat. No. 6,555,135 describes co-micronized mixture of fenofibrate with pharmaceutically acceptable excipient that is not a surfactant.

U.S. Pat. Nos. 6,074,670 and 6,277,405 disclose micronized fenofibrate coated onto hydrosoluble carriers with optional surface-active agents.

U.S. Pat. No. 6,828,334 describes inclusion complex of fenofibrate with cyclodextrins.

U.S. Pat. No. 6,027,747 describes solid dispersion of fenofibrate.

U.S. Patent Application No. 20040087656 describes fenofibrate of particle size less than 2000 nm with an improved bioavailability.

U.S. Patent Application Nos. 20060222706 and 20060222707 describe fenofibrate in intimate association with menthol or surfactant mixture.

U.S. Patent Application No. 20030138496 micronized fenofibrate with inert hydrosoluble carriers.

Several other patents and applications describe specific formulations of micronized fenofibrate with specific polymeric or surface-active agent additives while several others describe emulsion and suspension formulations of fenofibrate.

The solubility of an active pharmaceutical ingredient influences the bioavailability of the drug. Fenofibrate is a poorly soluble drug. Due to its poor hydrosolubility, fenofibrate poses problem of low dissolution. It is also poorly absorbed in the digestive tract and consequently its bioavailability is incomplete and irregular. Clearly, there is a need for improved compositions in which the fenofibrate exhibits better dissolution properties.

SUMMARY OF THE INVENTION

In one general aspect there is provided a pharmaceutical composition comprising unmicronized fenofibrate or a salt thereof in admixture with one or more wetting agents and one or more pharmaceutically acceptable excipients, wherein the admixture is not comicronized before processing.

In another general aspect of the invention there is provided a process for preparing a pharmaceutical composition of fenofibrate. The process includes:
a) mixing unmicronized fenofibrate with one or more wetting agents and optionally with other pharmaceutically acceptable excipients;
b) converting the pre-mix of step a) into granules; and
c) converting the granules of step b) into a suitable dosage form.

In another general aspect of the invention there is provided a pharmaceutical composition comprising unmicronized fenofibrate or a salt thereof in admixture with one or more wetting agents and one or more pharmaceutically acceptable excipients, wherein the mixture is not comicronized before processing and wherein the formulation exhibits a dissolution profile such that more than 75% of fenofibrate is released within first 30 minutes, wherein the release rate is measured in Apparatus 2 (USP, Dissolution, paddle, 50 rpm) using 1000 ml of 0.05M SLS in water at 37° C.±0.5° C.

Embodiments of the pharmaceutical composition may include one or more of the following features. For example, the pharmaceutically acceptable excipients may include one or more of fillers, binders, lubricants, sweeteners, coloring and flavoring agents, glidants, disintegrants, and the like.

The details of one or more embodiments of the inventions are set forth in the description below. Other features, objects and advantages of the inventions will be apparent from the description and claims.

DETAILED DESCRIPTION OF THE INVENTION

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

The information provided below is not admitted to be prior art to the present invention, but is provided solely to assist the understanding of the reader. The details of one or more embodiments of the invention are set forth in the accompanying drawings and the description below. Other features, objects, and advantages of the invention will be apparent from the description and drawings, and from the claims.

Fenofibrate is practically insoluble in water. This insolubility characteristic causes fenofibrate to exhibit a low rate of dissolution in aqueous media, e.g., gastrointestinal fluids, which results in inadequate bioavailability after oral ingestion. The inventors while working on the fenofibrate formulation have surprisingly found that when fenofibrate is mixed with a wetting agent, it results in increased solubility of fenofibrate in aqueous fluids which in turn leads to significant increase in bioavailability. It was further observed that there is no need to co-micronize the mixture to increase the surface area.

Suitable wetting agents may be one or more of anionic, cationic or non-ionic surface-active agents or surfactants. Wetting agent may further include one or more of gum acacia, guar gum, xanthan gum, kaolin, bentonite, hectorite, tragacanth, sodium alginate, pectin, and the like.

Suitable anionic surfactants may be one or more of sodium dodecyl sulfate (SDS), sodium lauryl sulfate (SLS), sodium laurate, dialkyl sodium sulfosuccinates, sodium stearate, potassium stearate, sodium oleate, and the like.

Suitable cationic surfactants may be one or more of benzalkonium chloride, bis-2-hydroxyethyl oleyl amine, benzethonium chloride, cetrimide, and the like.

Suitable non-ionic surfactants may be one or more of poloxamers, polyoxyethylene sorbitan fatty acid esters, fatty alcohols such as lauryl, cetyl and stearyl alcohols; glyceryl esters such as the naturally occurring mono-, di-, and triglycerides; fatty acid esters of fatty alcohols and other alcohols such as propylene glycol, polyethylene glycol, sorbitan, sucrose, cholesterol, and the like.

The term unmicronized fenofibrate as used herein refers to fenofibrate which is used as such and not subjected to size reduction by any means.

The pharmaceutical composition of the invention can be present in the form of a tablet, capsule, powder, disc, caplet, granules, pellets and other dosage forms suitable for oral administration. The tablets may further be coated with film forming polymers.

Examples of some film forming polymers that can be used for the coating include but are not limited to those known in the art, such as cellulose derivatives (hydroxypropyl methylcellulose, hydroxyethylcellulose, hydroxypropyl cellulose and their derivatives), acrylic and methacrylic copolymers of different molecular weights, and mixtures thereof.

The coating layers over the tablet may be applied as solution/dispersion of coating ingredients using conventional techniques known in the art selected from spray coating in a conventional coating pan or fluidized bed processor, dip coating, and the like.

The pharmaceutical compositions may include one or more pharmaceutically acceptable excipients from fillers, binders, lubricants, sweeteners, coloring and flavoring agents, glidants, disintegrants, and the like.

Suitable fillers may be one or more of microcrystalline cellulose, mannitol, calcium phosphate, calcium sulfate, kaolin, dry starch, powdered sugar, and the like.

Suitable binders may be one or more of povidone, starch, stearic acid, gums, hydroxypropylmethyl cellulose, and the like.

Suitable lubricants may be one or more of magnesium stearate, zinc stearate, calcium stearate, stearic acid, sodium stearyl fumarate, hydrogenated vegetable oil, glyceryl behenate, and the like.

Suitable glidants may be one or more of colloidal silicon dioxide, talc or cornstarch and the like.

Suitable disintegrants may be one or more of starch, croscarmellose sodium, crospovidone, sodium starch glycolate, and the like.

The pharmaceutical composition of the invention can be prepared by mixing fenofibrate with one or more wetting agents, compacting the pre-mix through a compactor and sizing the flakes into granules. The granules thus obtained may be granulated with a binder, dried, mixed with other pharmaceutically acceptable excipients, or granules may be directly mixed with other pharmaceutically acceptable excipients, lubricated and compressed.

The pharmaceutical composition comprising unmicronized fenofibrate or a salt thereof in admixture with one or more wetting agents and one or more pharmaceutically acceptable excipients, wherein the mixture is not comicronized before processing; and wherein the formulation exhibits a dissolution profile such that more than 75% of fenofibrate is released within first 30 minutes, wherein the release rate is measured in Apparatus 2 (USP, Dissolution, paddle, 50 rpm) using 1000 ml of 0.05M SLS in water at 37° C.±0.5° C.

Other embodiments are encompassed by this inventions. In one embodiment, the invention is directed to a pharmaceutical composition comprising unmicronized fenofibrate or a salt thereof in an admixture.

In another embodiment, the invention is directed to a pharmaceutical composition comprising unmicronized fenofibrate or a salt thereof in admixture with one or more wetting agents and one or more pharmaceutically acceptable excipients, wherein the admixture is not comicronized before processing.

In another embodiment, the invention is directed to a pharmaceutical composition comprising unmicronized fenofibrate or a salt thereof; wherein the composition further comprises poloxamer, lactose, silicified microcrystalline cellulose, crospovidone, povidone, purified water, magnesium stearate, and opadry.

In a preferred embodiment, the fenofibrate is present in the pharmaceutical composition in an amount of about 20-70% (w/w).

In a preferred embodiment, the composition further comprises poloxamer which is present in the pharmaceutical composition in an amount of about 5-50% (w/w).

In a preferred embodiment, the composition further comprises lactose which is present in the pharmaceutical composition in an amount of about 20-70% (w/w).

In a preferred embodiment, the composition further comprises silicified microcrystalline cellulose which is present in the pharmaceutical composition in an amount of about 5-70% (w/w).

In a preferred embodiment, the composition further comprises crospovidone which is present in the pharmaceutical composition in an amount of about 1-6% (w/w).

In a preferred embodiment, the composition further comprises povidone at about 0.1-10% (w/w).

In a preferred embodiment, the composition further comprises purified water (q.s).

In a preferred embodiment, the composition further comprises magnesium stearate which is present in the pharmaceutical composition in an amount of about 0.1-3% (w/w).

In a preferred embodiment, the composition further comprises opadry which is present in the pharmaceutical composition in an amount of about 0.5-5% (w/w).

In another embodiment, the invention is a pharmaceutical composition comprising unmicronized fenofibrate or a salt thereof in an admixture; wherein the fenofibrate which is present in the pharmaceutical composition in an amount of about 20-70% (w/w), poloxamer is present in the pharmaceutical composition in an amount of about 5-50% (w/w), lactose which is present in the pharmaceutical composition in an amount of about 20-70% (w/w), silicified microcrystalline cellulose which is present in the pharmaceutical composition in an amount of about 5-70% (w/w), crospovidone which is present in the pharmaceutical composition in an amount of about 1-6% (w/w), povidone which is present in the pharmaceutical composition in an amount of about 0.1-10% (w/w), purified water (q.s), magnesium stearate which is present in the pharmaceutical composition in an amount of about 0.1-3% (w/w), and opadry which is present in the pharmaceutical composition in an amount of about 0.5-5% (w/w).

In another embodiment, the invention is directed to a pharmaceutical composition comprising unmicronized fenofibrate or a salt thereof in an admixture wherein the admixture further comprises; poloxamer, lactose, silicified microcrystalline cellulose, crospovidone, povidone, purified water, magnesium stearate, opadry, or a mixture of two or more thereof.

In another embodiment, the invention is directed to a pharmaceutical composition comprising unmicronized fenofibrate or a salt thereof in an admixture wherein the admixture further comprises; fenofibrate which is present in an amount of about 20-70% (w/w), poloxamer which is present in an amount of about 5-50% (w/w), lactose which is present in an amount of about 20-70% (w/w), silicified microcrystalline cellulose which is present in an amount of about 5-70 (% w/w), crospovidone which is present in an amount of about 1-6% (w/w), povidone which is present in an amount of about 0.1-10% (w/w), purified water (q.s), magnesium stearate which is present in an amount of about 0.1-3% (w/w), opadry which is present in an amount of about 0.5-5% (w/w), or a mixture of two or more thereof.

The invention is further illustrated by the following examples which are provided merely to be exemplary of the invention and do not limit the scope of the invention. Certain modifications and equivalents will be apparent to those skilled in the art and are intended to be included within the scope of the invention.

Example 1

The composition of batches is provided in Table 1. Following formulations are representatives of the preferred compositions of the invention. The preparation of example 1 is detailed below.

TABLE 1

Composition of Fenofibrate Tablets (48 mg, 145 mg)

| Sr. No. | Ingredients | Qty/tablet (% w/w) |
|---|---|---|
| | Part-I | |
| 1 | Fenofibrate (unmicronized) | 20-70 |
| 2 | Poloxamer | 5-50 |
| | Part-II | |
| 4 | Lactose | 20-70 |
| 5 | Silicified microcrystalline cellulose | 5-70 |
| 6 | Crospovidone | 1-6 |
| 7 | Povidone | 0.1-10 |
| 8 | Purified water | q.s. |
| 9 | Magnesium stearate | 0.1-3 |
| 10 | Opadry | 0.5-5 |

Procedure: Unmicronized fenofibrate and poloxamer were co-sifted and mixed in a double cone blender. The above pre-mix was compacted through a roll compactor and sizing was carried out to break flakes in to granules using a multi mill or oscillating granulator. The granules thus obtained were blended with pre-sifted lactose, silicified microcrystalline cellulose, crospovidone in a rapid mixer granulator and granulated with a binder solution in a rapid mixer granulator. The granules were dried, milled and blended with pre-sifted crospovidone. The granules were then lubricated with magnesium stearate and the final blend was compressed in to tablets using suitable tooling and coated with aqueous dispersion of Opadry.

Example 2

The composition of the batches is provided in Table 2. Following formulations are representatives of the preferred compositions of the invention. The preparation of example 2 is detailed below.

TABLE 2

Composition of Fenofibrate Tablets (48 mg, 145 mg)

| Sr. No. | Ingredients | Qty/tablet (% w/w) |
|---|---|---|
| | Part-I | |
| 1 | Fenofibrate (unmicronized) | 20-70 |
| 2 | Poloxamer | 5-50 |
| | Part-II | |
| 4 | Lactose | 20-70 |
| 5 | Silicified microcrystalline cellulose | 5-70 |
| 6 | Crospovidone | 1-6 |
| 7 | Magnesium stearate | 0.1-3 |
| 8 | Opadry | 0.5-5 |

Procedure: Unmicronized fenofibrate and poloxamer were co-sifted and mixed in a double cone blender. The above pre-mix was compacted through a roll compactor and sizing was carried out to break flakes in to granules using a multi mill or oscillating granulator. The granules thus obtained were blended with pre-sifted lactose, silicified microcrystalline cellulose, crospovidone in a double cone blender and lubricated with magnesium stearate and the final blend was compressed in to tablets using suitable tooling and coated with aqueous dispersion of Opadry.

TABLE 3

Dissolution data of Fenofibrate tablets (145 mg)
Table 3 provides the dissolution data for fenofibrate tablets (145 mg) prepared as per the Formula given in Table 1 and 2. For determination of drug release rate, USP Type 2 Apparatus (rpm 50) was used wherein 1000 ml of 0.05M SLS in water at 37° C. ± 0.5° C. was used as medium.

| Time (min) | % drug released (Example-I) | % drug released (Example-II) |
|---|---|---|
| 10 | 25 | 31 |
| 20 | 60 | 66 |
| 30 | 80 | 83 |
| 45 | 92 | 96 |

While the invention has been described in terms of its specific embodiments, certain modifications and equivalents will be apparent to those skilled in the art and are intended to be included within the scope of the invention.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A pharmaceutical composition comprising unmicronized fenofibrate or a salt thereof wherein the composition further comprises poloxamer, lactose, silicified microcrystalline cellulose, crospovidone, povidone, magnesium stearate, and opadry.

2. A pharmaceutical composition comprising unmicronized fenofibrate or a salt thereof wherein the composition further comprises poloxamer, lactose, silicified microcrystalline cellulose, crospovidone, povidone, purified water, magnesium stearate, and opadry.

3. A pharmaceutical composition comprising unmicronized fenofibrate or a salt thereof in an admixture; wherein the fenofibrate is present in an amount of about 20-70% (w/w), the poloxamer is present in an amount of about 5-50% (w/w), lactose is present in an amount of about 20-70% (w/w), silicified microcrystalline cellulose is present in an amount of about 5-70% (w/w), crospovidone is present in an amount of about 1-6% (w/w), povidone is present in an amount of about 0.1-10% (w/w), purified water (q.s), magnesium stearate is present in an amount of about 0.1-3% (w/w), and opadry is present in an amount of about 0.5-5% (w/w).

4. A process for the preparation of a pharmaceutical composition of claim 3, wherein the process comprising: a. mixing unmicronized fenofibrate with one or more wetting agents and optionally with one or more pharmaceutically acceptable excipients; b. converting the pre-mix of step a) in to granules; and c. converting the granules of step b) in to a suitable dosage form.

5. The process of claim 4, wherein the wetting agent comprises one or more of a surface-active agent, gum acacia, guar gum, xanthan gum, kaolin, bentonite, hectorite, tragacanth, sodium alginate, and pectin.

6. The process of claim 5, wherein the surface-active agent is anionic, cationic, or non-ionic.

7. The process of claim 4, wherein the pharmaceutically acceptable excipients comprises one or more from fillers, binders, lubricants, sweeteners, coloring and flavoring agents, glidants, and disintegrants.

* * * * *